(12) United States Patent
Pothier

(10) Patent No.: US 6,201,167 B1
(45) Date of Patent: Mar. 13, 2001

(54) PRODUCTION OF RECOMBINANT PROTEINS IN SEMEN

(75) Inventor: François Pothier, St-Lambert de Lévis (CA)

(73) Assignee: Universite Laval, Quebec (CA)

( * ) Notice: Subject to any disclaimer, the term of this patent is extended or adjusted under 35 U.S.C. 154(b) by 0 days.

(21) Appl. No.: 09/237,974

(22) Filed: Jan. 27, 1999

Related U.S. Application Data

(63) Continuation-in-part of application No. 08/825,955, filed on Apr. 3, 1997.

(51) Int. Cl.$^7$ .............................. A01K 67/00; C12P 21/00
(52) U.S. Cl. ................................ 800/18; 800/4; 435/69.1
(58) Field of Search .................................. 800/13, 18, 4; 435/69.1

(56) References Cited

FOREIGN PATENT DOCUMENTS

WO 94 03594    2/1994  (WO) .

OTHER PUBLICATIONS

Kappell et al (1992) Current Opinion in Biotechnology 3, 548–553.*
Wall (1996) Theriogenology 45, 57–68.*
Southard Smith, M. et al., "Tissue–specific expression of kallikrein family transgenes in mice and rats", DNA and Cell Biology, vol. 11, No. 5, Jun. 1992, pp. 345–358.
Schaffner, D. L. et al., "Transgenic mice carrying a PSA-rasT24 hybrid gene develop salivary gland and gastrointestinal tract neoplasms", Laboratory Investigation, vol. 72, No. 3, Mar. 1995, pp. 283–290.

Wei, C. et al. "Development of human PSA–expressing transgenic mice to investigate targeted CTL–mediated immunity for prostate cancer", Faseb Journal, vol. 10, No. 6, 1996, p. a1467.

Wei, C. et al., "Tissue–specific expression of the human prostate–specific antigen gene in transgenic mice implications for tolerance and immunotherapy ", Proceedings of the National academy of Sciences of USA., vol. 94,No. 12, Jun. 1997, pp. 6369–6374.

Cleutjens, K.B. J.M. et al., "A 6–kb promoter fragment mimics in transgenic mice the prostate–specific and androgen regulated expression of the endogenous prostate–specific antigen gene in humans", Molecular Endocrinology, vol. 11, No. 9, Aug. 1997, pp. 1256–1265.

* cited by examiner

*Primary Examiner*—Deborah Crouch
(74) *Attorney, Agent, or Firm*—Sawbey Ogilvy Renault; France Côté

(57) ABSTRACT

The present invention relates to a method for the production and secretion into animal's semen of an exogenous recombinant protein comprising the steps of: a) producing a non-human transgenic animal characterized by an expression system comprising a promoter specific for the genital tract or accessory glands operatively linked to an exogenous DNA sequence coding for the recombinant protein through a DNA sequence coding for a signal peptide effective in secreting and maturing the recombinant protein in genital tract tissue; b) collecting semen produced by the non-human transgenic animal; and c) isolating the exogenous recombinant protein from the semen.

6 Claims, 4 Drawing Sheets

FIG_2

PRODUCTION OF RECOMBINANT PROTEINS IN SEMEN

RELATED APPLICATIONS

This application is a continuation-in-part of applications Ser. No. 08/825,955 filed on Apr. 3, 1997 which is still pending and the content of which is incorporated by reference.

BACKGROUND OF THE INVENTION (a) Field of the Invention

The invention relates to the production of recombinant proteins in animal's semen using the seminal gland as a bioreactor. Particularly, this invention relates to an expression system which comprises at least a semen-specific protein promoter operatively linked to a DNA sequence coding for a signal peptide and a desired recombinant protein product. When such a system is transgenically incorporated into an animal, the recombinant protein is expressed in the semen of the animal. This invention also relates to the transgenic animal that produces the desired recombinant product in its semen. Recombinant products produced by the expression systems and transgenically altered animals of this invention can be produced at significantly less cost than by conventional recombinant protein production techniques. There is also a potential to alter specific characteristics related to sperm viability and potential storage systems.

(b) Description of Prior Art

Recombinant DNA technology has enabled the cloning and expression of genes encoding medically and agriculturally important proteins and glycoproteins. Such products include, "for example, insulin, growth hormone, growth hormone releasing factor, somatostatin, tissue plasminogen activator, tumor necrosis factor, lipocortin, coagulation factors VIII and IX, erythropoietin, the interferons, colony stimulating factor, the interleukins and urokinase, antibodies.

Many of these important proteins, however, are large (molecular weights in excess of 30 Kd), secreted, require sulfhydryl bonds to maintain proper folding, are glycosylated and are sensitive to proteases. As a result, the recombinant production of such products in prokaryotic cells has proven to be less than satisfactory because the desired recombinant proteins are incorrectly processed, lack proper glycosylation or are improperly formed. Accordingly, resort has been had to the production of those recombinant proteins in cultured eukaryotic cells. This technique has proven to be both expensive and often unreliable due the variability of cell culture methods. For example, average yields are 10 mg of recombinant protein per liter of culture media, with the resulting cost typically for exceeding one thousand dollars per gram of recombinant protein. Accordingly, resort has been had to the production of those recombinant proteins in cultured eukaryotic cells. It is believed that the use of the genital tract as a tissue for expression overcomes, either wholly or to a satisfactory degree, this potential source of difficulty. Several examples using mammary glands of transgenic mammals as bioreactors have demonstrated their potential to produce recombinant protein products.

Harvesting from body fluids as opposed to solid tissue is desirable, because such routes, are by and large renewable, and most proteins of biomedical importance are themselves secreted into body fluids. Secretion into the bloodstream is a possible route, either from liver or B lymphocytes, but the coagulating properties of blood and the presence of biologically active peptides and antigenic molecules may prove a hindrance to subsequent downstream processing.

It would be highly desirable to be provided with a means to produce recombinant proteins in large quantities.

SUMMARY OF THE INVENTION

The above difficulties may be overcome in accordance with the present invention, as it is the case, for example, for the production of recombinant protein milk, by the use of the genital tract as a tissue of expression. Semen is readily collected, available in large quantities in several animal species and well characterized biochemically. Further, several proteins are present at high concentrations in this body fluid.

The present invention is a new method to solve such problems by providing an efficient means of producing large quantities of recombinant protein products in the semen of transgenically altered animals.

According to one embodiment of the present invention, a DNA sequence coding for a desired protein is operatively linked in an expression system to a genital tract-specific protein promoter, or any promoter sequence specifically activated in male genital tissue, through a DNA sequence coding for a signal peptide that permits secretion and maturation of the desired protein n the genital tract tissue. More preferably, the expression system also includes a 3' untranslated region downstream of the DNA sequence coding for the desired recombinant protein. This untranslated region may stabilize the rDNA transcript of the expression system. Optionally, the expression system also includes a 5' untranslated region upstream of the DNA sequence coding for the signal peptide.

The expression system is transgenetically introduced into a host genome. As a result, one or more copies of the construct or system become incorporated into the genome of the transgenic animal. The presence of the expression system will permit the male species to produce and to secrete the recombinant protein product, into or along with its semen. Such method permits the low cost, high level production of the desired proteins.

The expression "operatively linked" as used herein is intended to mean the linking of a genital tract-specific promoter or a promoter specifically activated in genital tract tissue to a DNA sequence coding for a desired protein so as to permit and control expression of that DNA sequence and production of that protein.

The expression "recombinant protein" as used herein is intended to mean a protein or peptide coded for by a DNA sequence which is not endogenous to the native genome of the animal in whose semen it is produced in accordance with this invention or a protein or peptide coded for by a DNA sequence which is endogenous to the native genome of the animal in whose semen it is produced does not lead to the production of that protein or peptide in its semen at the same level that the transgenic animal of this invention produces that protein in its semen.

The expression "genital tract" as used herein is intended to mean the reproductive anatomical male system whole or in part involving the prostate gland, the seminal vesicle, epididymis, seminiferous tubules, ampule, vas deferens, and the bulbourethral gland.

In accordance with the present invention there is provided a method for the production and secretion into a non-human animal's semen of an exogenous recombinant protein comprising the steps of:

a) producing a non-human transgenic animal characterized by an expression system comprising a promoter specific for the genital tract or accessory glands operatively linked to an exogenous DNA sequence coding for the recombinant protein through a DNA sequence coding for a signal peptide effective in secreting and maturing the recombinant protein in genital tract tissue;

b) collecting semen produced by the non-human transgenic animal; and c) isolating the exogenous recombinant protein from the semen.

The expression system used in accordance with the present invention may also include a 3' untranslated region downstream of the DNA sequence coding for the recombinant protein or a 5' untranslated region between the promoter and the DNA sequences coding for the signal peptide.

In accordance with another embodiment of the present invention, the promoter may be selected from the group consisting of p12, p25, kallikreins, PSA, SBP-C and secretory protein IV promoters.

In accordance with another embodiment of the present invention, the recombinant protein may be selected from the group consisting of mono- and bi-specific antibodies, immunoglobulins, cytokines, coagulation factors, tissue plasminogen activator, GM-CSF, erythropoietin, thrombopoietin, alpha-1 anti-trypsin, animal growth hormones, cell surface proteins, insulin, interferons, lipases, antiviral protein, antibacterial protein, bacteriocins, peptide hormones, lipocortins and epidermal growth factor.

In accordance with another embodiment of the present invention, there is provided a method to increase sperm viability and semen storage which comprises the steps of:

a) producing a non-human transgenic animal characterized by an expression system comprising a promoter specific for the genital tract or accessory glands operatively linked to an exogenous DNA sequence coding for a recombinant protein capable of improving sperm viability and semen storage through a DNA sequence coding for a signal peptide effective in secreting and maturing the recombinant protein in genital tract tissue; and b) collecting semen produced by the non-human transgenic animal; whereby the semen has an improved storage capability and containing sperms of increased viability.

In accordance with another embodiment of the present invention, the recombinant protein may be selected from the group consisting of catalase, super-oxide dismutase, calcitonin, antibiotics such as gentamycin, and epididymal fertility proteins.

DETAILED DESCRIPTION OF THE INVENTION

Figure 1:
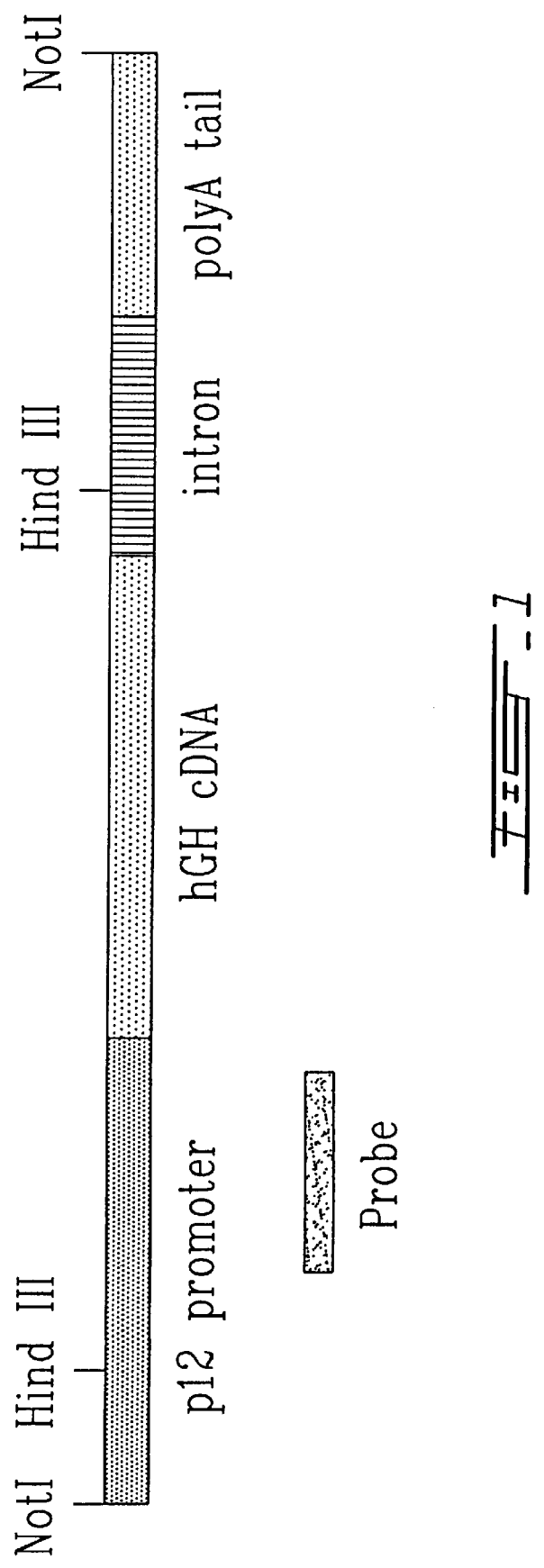
FIG. 1 illustrates a chimeric construct containing the mouse p12 gene promoter linked to the human growth hormone coding sequence in accordance with one embodiment of the present invention.

In accordance with the present invention, the seminal gland of non-human transgenic animal is used as a bioreactor to produce recombinant protein.

The present invention solves such problems by providing new efficient means of producing large quantities of recombinant protein products in the semen of transgenically altered animal.

More precisely, this invention relates to processes, DNA sequences, compositions of matter and transgenic animals for the production of recombinant proteins. More specifically, this invention relates to the transgenic incorporation of one or more copies of a construct comprising a genital tract-specific protein promoter or any promoter sequence specifically activated in genital tract tissue, operatively linked to a DNA sequence coding for a desired recombinant protein through a DNA sequence coding for a signal peptide that permits the secretion and maturation of the desired recombinant protein in the genital tract tissue. The construct is transgenically incorporated into animal embryos or stem cells or adult cells used for cloning and the recombinant protein product is subsequently expressed and secreted into or along with the semen of the transgenic animal.

Any animal may be usefully employed in this invention. Preferably, animal that produce large volumes of semen and have frequent ejaculating periods are preferred. Preferred animal are mammals, such as pigs. of course, each of these animals may not be as effective as the others with respect to any given expression sequence of this invention. For example, a particular genital tract-specific promoter or signal sequence may be more effective in one animal than in others. However, one of skill in the art may easily make such choices by following the teachings of this invention.

Among the genital tract-specific protein promoters useful in the various embodiments of this invention are the p12, p25, kallikreins, PSA, SBP-C and secretory protein IV promoters. The genital tract specific protein promoter or the promoters that are specifically activated in genital tract tissue may be derived from either cDNA or genomic sequences. Preferably, they are genomic in origin.

Among the signal peptides that are useful in accordance with this invention are genital tract-specific signal peptides or other signal peptides useful in the secretion and maturation of eukaryotic and prokaryotic proteins. Preferably, the signal peptide is selected from genital tract-specific signal peptides or signal peptide of the desired recombinant protein product, if any. Most preferably, the genital tract-specific signal peptide is related to the genital tract-specific promoter used in the expression system of this invention. The size of the signal peptide is not critical for this invention. All that is required is that the peptide be of a sufficient size to effect secretion and maturation of the desired recombinant protein in the genital tract tissue where it is expressed.

Among the protein products which may be produced by the processes of this invention include, for example, mono- or bi-specific antibodies, immunoglobulins, cytokines, coagulation factors, tissue plasminogen activator. GM-CSF, erythropoietin, thrombopoietin, alpha-1 antitrypsin, animal growth hormones, cell surface proteins, insulin, interferons, lipases, antiviral protein, antibacterial protein, bacteriocins, peptide hormones, lipocortins and other recombinant protein products.

The desired recombinant protein may be produced as a fused protein containing amino acids in addition to those of the desired or native protein. For example, the desired recombinant protein of this invention may be produced as part of a larger recombinant protein in order to stabilize the desired protein or to make its purification from semen easier and faster. The fusion is then broken and the desired protein isolated. The desired recombinant protein may alternatively be produced as a fragment or derivative of native protein or it may be produced having an amino acid sequence similar to the native protein. Each of these alternatives is readily produced by merely choosing the correct DNA sequence.

Preferably, the expression system or construct of this invention also includes a 3' untranslated region downstream of the DNA sequence coding for the desired recombinant protein. This region apparently stabilizes the RNA transcript of the expression system and thus increases the yield of desired protein from the expression system. Among the 3' untranslated regions useful in the constructs of this invention are sequences that provide a poly A signal. Such sequences may be derived, for example, from the SV40 small t antigen, the bovine growth hormone 3' untranslated region or other 3' untranslated region known in the art. Preferably, the 3' untranslated region is derived from a semen protein. The length of the 3' untranslated region is not critical but the stabilizing effect of its poly A transcript appears important in stabilizing the RNA of the expression sequence.

Optionally, the expression control sequences of this invention also include a 5' untranslated region between the promoter and the DNA sequence encoding the signal peptide. Such untranslated regions are preferably related to the promoter. However, they may be derived from other synthetic, semi-synthetic and natural sources. Again their specific length is not critical, however, they appear to be useful in improving the level of expression.

The above-described expression systems may be prepared using methods well known in the art. For example, various ligation techniques employing conventional linkers, restriction sites etc., may be used to good effect. Preferably, the expression system of this invention are prepared as part of larger plasmids. Such preparation allows the cloning and selection of the correct constructions in an efficient manner as is well known in the art. Most preferably, the expression systems of this invention are located between convenient restriction sites on the plasmid so that they can be easily isolated from the remaining plasmid sequences for incorporation into the desired animal.

After such isolation and purification, the expression systems or constructs of this invention are added to the gene pool of the animal which is to be transgenically altered. For example, one or several copies of the construct may be incorporated into the genome of an animal embryo by standard or new transgenic techniques. One animal which has been shown to produce up to 500 ml of semen at each two days in pig, almost as much fluid as goat or sheep milk by day. This appears to be an animal of choice for the production of recombinant proteins of interest in the semen.

One technique for transgenically altering an animal is to microinject the construct into the pronuclei of the fertilized animal egg(s) to cause one or more copies of the construct to be retained in the cells of the developing animal(s). Usually, transgenic animals contain at least one copy of the cloned construct in somatic tissues and transmit the gene through the germ line to the next generation. The progeny of the transgenically manipulated embryos may be tested for the presence of the construct by Southern blot analysis of a biopsy of tissue or amplification of a transgene sequence by polymerase chain reaction technique. If one or more copies of the exogenous cloned construct remains stably integrated into the genome of such transgenic embryos, it is possible to establish permanent transgenic animal lines carrying the transgenically added construct.

The litters of transgenically altered animals may be assayed after birth for the incorporation of the construct into the genome of the offspring. Preferably, this assay is accomplished by hybridizing a probe corresponding to the DNA sequence coding for the desired recombinant protein product or a segment thereof onto chromosomal material from the progeny. Those animal progeny found to contain at least one copy of the construct in their genome are grown to maturity. The male species of these progeny will produce the desired protein or along with their semen. Alternatively, the transgenic animal may be bred to produce other transgenic progeny useful in producing the desired proteins in their semen.

The ability to introduce and express exogenous genetic information in the context of a developing organism allows the investigation of the mechanisms regulating specific gene expression and the role of such expression in normal development and pathological states. Since the first success at producing transgenic mice using microinjection of eggs with cloned genes (Gordon et al., 1980, *Proc. Natl. Acad. Sci. USA* 77:7380–7384), numerous investigators have employed this technique to study various developmental processes. The use of transgenic mice to study gene regulation has steadily increased, and is considered as a "must" in evaluating DNA constructs before to produce transgenic farm animals with it.

Production of recombinant proteins in mammary glands of transgenic animals can be considered as a good example to point out that mouse model serves not only to study the correct functionality of DNA constructs. Moreover, it demonstrates clearly, respecting some basic rudiments of "tissue specificity", it is of general rule that there is a reasonable direct correlation between the manner a transgene works in mouse and the manner the same transgene works in other animals, namely farm animals.

A number of milk protein genes have been shown to express in the mammary gland of transgenic mice, including the rat whey acidic protein (WAP) gene (Bayna and Rosen, 1990, *Nuc. Acid. Res.* 18:2977–2985), rat β-casein (Lee et al., 1989, *Nuc. Acid. Res.* 16:1027–1045), and bovine α-lactalbumin (Vilotte et al., 1990, *Eur. J. Biochem.* 186: 43–48). Better again, Wall et al., (1991, *Proc. Natl. Acad. Sci. USA*, 88:1696–1700) have shown that the mouse WAP gene expresses efficiently in the mammary gland of transgenic pigs.

Tissue-specific expression of DNA encoding various proteins in the mammary gland or the production of various proteins in the milk of transgenic mice and sheep have been reported in a number of laboratories. For example, Simons et al. (1987, *Nature* 328:530–532) report the microinjection of the ovine β-lactoglobulin (BLG) encoding sequence with its own promoter into fertilized mouse eggs. According to these authors, the sheep BLG was expressed n mammary tissue and produced BLG in the milk of the transgenic mice. When the cDNA encoding human factor IX or human α1-antitrypsine was inserted into the promoter of the sheep BLG gene and microinjected into sheep (Simmons et al., 1988, *Bio/Technology* 6:179–183) the production of factor IX and α1-antitrypsin was again observed.

Human tissue plasminogen activator (t-PA) reportedly was produced in transgenic mouse milk when a cDNA encoding a human t-PA with its endogenous signal sequence was expressed under control of the murine WAP promoter (Gordon et al., 1987, Bio/Technology 5:1183–1187). The same experiment has been repeated by Pittius et al., (1988, Proc. Natl. Acad. Sci. USA 85:5874–5878).

There is disclosed in U.S. Pat. No. 4,873,316 issued on Oct. 10, 1989, the use of 9 kb of 5' sequence from the bovine aS1 casein gene including the casein signal peptide and several casein codons fused to a mature human t-PA sequence. The transgenic mice obtained with this construct reportedly produced appreciable amounts of a t-PA fusion protein in their milk. Production of transgenic cows with the same construct were shown in this patent.

In addition, a number of patent publications purportedly describe the production of specific proteins in the milk of transgenic mice and sheep. European Patent No. 0 264 166 published on Apr. 20, 1988 relates to hepatitis B surface antigen and t-PA genes under control of the whey acid promoter for mammary tissue specific expression in mice. International patent application (PCT) published on Jan. 14, 1988 under No. WO 88/00239 discloses tissue specific expression of a transgene encoding human factor IX under control of an ovine β-lactoglobulin promoter in sheep. International patent application (PCT) published on Mar. 10, 1988 under No. WO88/01648 describes the use of the promoter in transgenic bovine, but make a demonstration only in mice (transgenic mouse having mammary secretory cells incorporation a recombinant expression system comprising a bovine a-lactalbumin gene fused to interleukin-2). International patent application (PCT) published on Dec. 29, 1988 under No. WO 88/10118, shows also only the mouse model (transgenic mice and sheep containing transgene encoding bovine αS1 casein promoter and signal sequence to t-PA). International patent application (PCT) published on Dec. 20, 1994 under No. WO 95/17085 shows the production of human antibodies under control of the goat β-casein promoter in mammary glands of transgenic mice (Production of antibodies in mammal's milk, through the creation of transgenic animals that selectively express foreign genes in mammary epithelial cells).

International patent application (PCT) published on Jun. 15, 1993 under PCT No. WO 93/25567 discloses the production of human lactoferrin, serum albumin, protein C, lysozyme and immunoglobulins under control of the bovine αS1 casein, β-lactoglobulin, and human lactoferrin promoters in mammary glands of transgenic mice. Based on their results obtained with the mouse model, the inventors of the latter patent find reasonable the extrapolation to the production of human cholesterol hydrolase, industrial enzymes, human Factor VIII, human Factor IX, protease, lipases, chitinases and ligninases, optionally under control of the bovine κ casein and αS2 casein promoters, without any demonstration.

The secretory cells of the mammary glands of several currently used laboratory and farm mammalian species have all the capacity to perform similarly most necessary post-translational processes to produce recombinant molecules under an active form. As example, the human protein C, a zymogen of serine protease is formed from post-translational cleavages that result in the removal of the signal and propeptide sequences. In addition, a dipeptide at amino acid positions 156–157 is removed in 70 to 95% of hPC molecules to yield a heterodimer containing a 41000 Mr heavy chain and a 21000 Mr light chain. Activation of hPC results from the proteolytic removal of the heavy chain. HPC possesses four different potential sites for N-linked glycosylation. In addition, hPC contains 12 intrachain disulfide brides, one β-hydrohylated aspartic acid residue, and nine gla residues. These gla residues occur within the first 29 amino acid residues of the light chain and are necessary for functional activity. Protein C is one of the most complex proteins to have been produced in transgenic mice and livestock and has thus presented a significant challenge to the porcine and mouse mammary glands in terms of protein processing. The studies (Morcol et al., 1992, Ann. N. Y. Acad. Sci. 665:218–233; Velander et al., 1992, Proc. Natl. Acad. Sci. USA 89:12003–12007; Velander et al., 1992, Ann. N. Y. Acad. Sci. 665:391–403), have demonstrated the ability of the porcine mammary gland to perform folding, disulfide bridging, proteolytic processing, glycosylation, and γ-carboxylation, which together result in a functional recombinant human protein.

Tables 1 and 2 below shows some references in which the use heterologous promoters to produce active recombinant proteins, endogenous or foreign. The references are divided in two categories: 1) The use of the transgenic mouse model to demonstrate the activity of heterologous promoters for production of foreign proteins; 2) The evidence of activity of heterologous promoters in farm animals to produce foreign proteins in different tissues.

TABLE 1

The use of the transgenic mouse model to demonstrate the activity of heterologous promoters for production of foreign proteins

| Promoter | Protein | References |
|---|---|---|
| Rat β-casein | rat β-casein | Lee et al., 1988 |
| Mouse WAP | Ha-ras oncogene | Andres et al., 1987 |
| Sheep β-lactoglobulin | sheep β-lactoglobulin | Simons et al., 1987 |
| Mouse WAP | human t-PA | Wright et al., 1991 |
| Rat β-casein | bacterial CAT reporter gene | Lee et al., 1990 |
| Rat WAP | rat WAP | Bayna et al., 1992 |
| Sheep β-lactoglobulin | human αl-antitrypsine | Archibald et al, 1991 |
| Bovine αS1-casein | human urokinase | Meade et al., 1990 |
| Goat β-cassein | human CFTR | DiTullio et al., 1992 |
| Bovine α-lactalbumin | bovine α-lactalbumin | Vilotte et al., 1989 |
| Goat α-lactalbumin | goat α-lactalbumin | Soulier et al., 1992 |
| Guinea-pig α-lactalbumin | guinea-pig α-lactalbumin | Maschio et al., 1991 |
| Goat β-casein | goat β-casein | Persuy et al., 1992 |
| Rat WAP | rat WAP | Dale et al., 1992 |
| Mouse WAP | breast cancer protein PS21 | Tomasetto et al 1991 |
| Mouse WAP | human t-PA | Pittius et al., 1988 |
| Mouse WAP | human t-PA | Gordon et al., 1987 |
| Mouse uroplakin | human growth hormone | Kerr et al., 1998 |
| Rat WAP | human Protein C | Wei et al., 1995 |

Abbreviations: WAP, whey acid protein; CFTR, cystic fibrosis transmembrane conductance regulator; t-PA, tissue plasminogen activator; CAT, chloramphenicol acetyl transferase.

TABLE 2

The evidence of activity of heterologous promoters in farm animals to produce foreign proteins in different tissues

| Promoter | Protein | Organ | References |
|---|---|---|---|
| PIG | | | |
| Mouse WAP | human protein C | mamm. gland | Morcol et al., 1992 |
| Mouse WAP | human protein C | mamm. gland | Velander et al., 1992 |
| Mouse MT | human GH | mamm. Gland | Hammer et al., 1985 |
| Mouse MT | bovine GH | mamm. Gland | Pursel et al., 1987 |
| Mouse MT | Human GHRH | mamm. Giand | Pursel et al., 1989 |
| Rat PEPCK | bovine GH | muscle | Wieghart |

TABLE 2-continued

The evidence of activity of heterologous promoters in
farm animals to produce foreign proteins in different tissues

| Promoter | Protein | Organ | References |
|---|---|---|---|
| Moloney leukemia virus | chicken ski | muscle | et al., 1990 Pursel et al., 1992 |
| Mouse WAP | mouse WAP | mamm. Gland | Shamay et al., 1991 |
| Human MT | porcine GH | mamm. Gland | Vize et al., 1988 |
| Moloney leukemia virus | rat GH | systemic | Ebert et al., 1988 |
| Mouse albumin | human GRF | systemic | Pursel et al., 1989 |
| Human CMV | pig GH | systemic | Ebert et al., 1990 |
| Mouse MT | human GH | mamm. gland | Brem et al., 1985 |
| Mouse Leukemia virus | porcine GH | systemic | Ebert et al., 1990 |
| Mouse sarcoma virus | chicken ski | muscle | Pursel et al., 1992 |
| CATTLE | | | |
| Mouse MT | bovine GH | mamm. gland | Roshlau et al., 1989 |
| Chicken skeletal actin | human ER | muscle | Massey et al., 1990 |
| Chicken skeletal actin | human IGF-1 | muscle | Hill et al., 1992 |
| Bovine αS1-casein | human lactoferrin | mamm. gland | Krimpenfort, 1991 |
| Mouse MTV | human IGF-1 | mamm. gland | Hill et al., 1992 |
| SHEEP | | | |
| Ovine β-lactoglobulin | human factor IX | mamm. gland | Clark et al., 1989 |
| Ovine β-lactoglobulin | human al-ATT | mamm. gland | Wright et al., 1991 |
| Mouse MT | bovine GH | mamm. gland | Hammer et al., 1985 |
| Mouse transferrin | bovine GH | mamm. gland | Rexroad et al., 1991 |
| Mouse albumin | human GHRH | systemic | Rexroad et al., 1991 |
| Sheep MT | sheep GH | mamm. gland | Nancarrow et al 1991 |
| Mouse MT | human GH | mamm. gland | Hammer et al., 1985 |

Abbreviations: MT, metallothionein; MTV, mammary tumor virus; CMV, cytomegalo virus; WAP, whey acid protein; PEPCK, phosphoenolpyruvat carboxy kinase; ATT, antitrypsine; GH, growth hormone; GHRH, growth hormone releasing hormone; GRF, growth releasing factor; IGF-1, insulin growth factor 1; ER, estrogen receptor.

Similarities in Semen Composition of Different Male Mammals

The biochemical characterization in fluid semen and protein of sperm surface of male mammals is still an obscure aspect in the field of animal reproduction physiology. However, data available at the moment regarding this aspect are in sufficient quantities to say that biochemical composition between different species in male mammals, namely between mouse and pig, are almost identical (Setchell, B. P., Maddocks, F. and Brooks, D. E. (1993) "Anatomy, vascularisation, inervation, and fluids of the male". In Physiology of reproduction. Ed. Knobil, E. Neill. Raben Press, N.Y., pp. 1063–1176). The results mentioned above in production of recombinant proteins in mammary glands of transgenic animals, and data regarding physiology of reproduction give together enough support to anticipate that recombinant protein produced in the male reproductive tract of transgenic mice under control of the p12 promoter will be produced in a highly similar manner in farm animals. The protein p12 is a member of a huge family of Kazal protease inhibitors known since at least 30 years, and secreted by the endothelium of genital tract of male mammalians and sexual accessory glands as the seminal vesicle. This protein has very high level of homology between mammalian species and its secretion is regulated in the same manner (reviewed by Laskowski, M. Jr. And Kato, I. (1980) Ann. Rev. Biochem. 49:593–666).

From the patents mentioned above and other references described in following tables, there are clear evidences to support the fact that other organs can be used to produce recombinant heterologous proteins and peptides. More evidently, a recent experiment have shown the possibility to use the bladder as a bioreactor by allowing the production of active human growth hormone into urine under control of the uroplakin promoter, a tissue specific promoter of bladder (Kerr et al., 1998, Nature Biotechnology 16:75–79).

The transgenic animal bioreactor industry has focused primarily on directing expression of their products to the milk, though at least one other organization has explored the possibility of isolating products from blood (Swanson et al., 1992, Bio/Technology 10:557–559). The present invention provides an alternative (i.e. using the genital tract and sexual accessory glands as a bioreactor) that has the same advantage of mammary gland bioreators: straightforward, noninvasive collection of the product.

We believe from data presented above that it is quite reasonable to extrapolate the results obtained in mice to other mamals, such as pigs.

The present invention will be more readily understood by referring to the following example which is given to illustrate the invention rather than to limit its scope.

EXAMPLE I

Production of Transgenic Mice

Transgene Construct

In order to test the efficiency of the concept, we have generated a chimeric construct in which the human growth hormone (hGH) cDNA was placed under the control of a 4 kb fragment of the p12 regulatory sequence from the mouse (FIG. 1). A poly A tail and an intron from the SV 40 virus were added to stabilize the messenger mRNA. The construct was excised from the vector by NotI digestion. For the southern blot analysis the genomic DNA was digested with HindIII which liberates a 5.2 kb fragment. The probe corresponds to a fragment of the p12 promoter.

This construct was cloned in the pPol III vector (plasmid) and amplified in E. coli. Since it has previously been shown that plasmid sequences impede transgene expression in a eukaryotic system, the resulting construct was isolated from the vector by a Not I digestion. The construction was ultra purified from the gel using a GenClean procedure and dissolved in Tris-HCl (5 mM)/EDTA(0.2 mM) buffer at a final concentration of 4 ng/ml.

Production of Transgenic Mice

Transgenic mice were generated by pronuclear microinjection of the construct into B6C/3F1 zygotes. Females were superovulated using one injection of PMSG (Pregnant mare serum gonadotrophin) followed by an injection of hCG (human chorionic gonadrotrophin) 46 hours later. After mating with a male of proven fertility, the female was sacrificed, the fertilized eggs isolated, observed under differential interference contrast optics of an inverted microscope and the most visible pronucleus microinjected with approximately 500 molecules of the transgene. After microinjection, the viable embryos were transferred to the oviduct of a pseudopregnant CD-1 female, obtained by mating with CD-1 vasectomised males.

Results

Identification of Transgenic Mice

Figure 2:
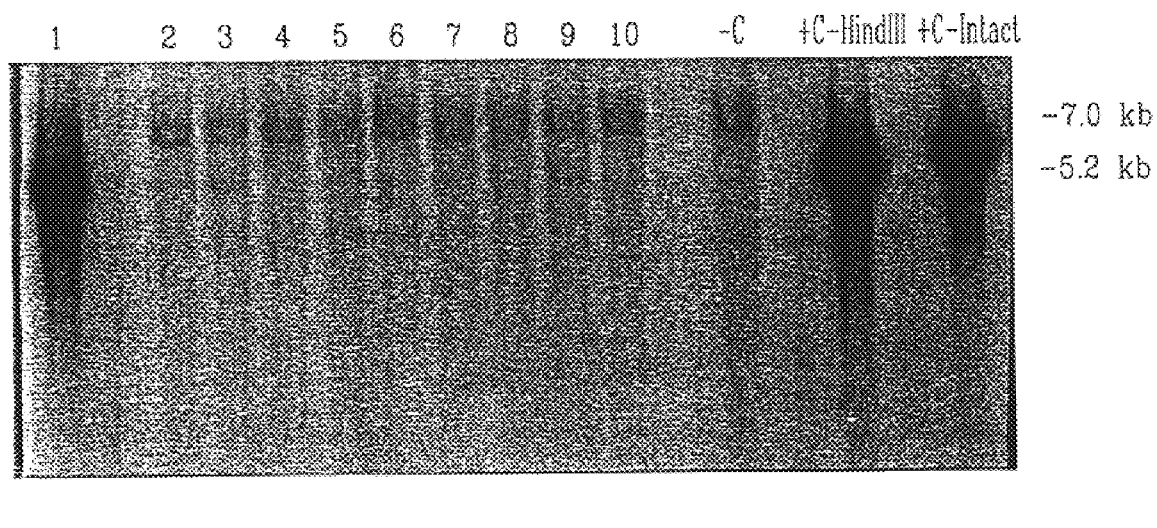
FIG. 2 illustrates a Southern blot analysis of the integration of the transgene into the genomic DNA of the transgenic mice.

One hundred embryos were microinjected and transferred in three pseudopregnant females. After 21 days, one litter of 7 pups, one of 2 pups and one of one pup were obtained. The screening for positive transgenic mice was performed by means of Southern blot analysis of HindIII-digested genomic DNA extracted from tail biopsies. DNA fragments were separated by electrophoresis on agarose gel and transferred to a nylon membrane. Blot hybridization was carried out using a 1 kb BamHI-fragment isolated from the p12 promoter, radiolabeled with [$\alpha$-$^{32}$p] dCTP by random priming. Hybridization was performed at 65° C. over 16 hours in a solution containing 6×SSC, 25 mM phosphate buffer (pH 7.2), 5×Denhardt's, 0.5% SDS, 1 mM EDTA (pH 8.0), and 100 ug/ml denatured salmon sperm DNA. Blots were then washed twice in 2×SSC and 0.1% SDS at room temperature for 15 min. and then in 0.1×SSC and 0.1% SDS at 60° C. for 30 min. and finally revealed with a PhosphoImager system. FIG. 2 shows the Southern blot analysis of the integration of the transgene into the genomic DNA of the transgenic mice. The probe derived from the p12 gene revealed an endogenous fragment of approximately 7 kb. This served as a control for the efficiency of the probe and provides an estimate of the amount of genomic DNA which was loaded in each well.

A specific band at 5.2 kb indicates that mice #1, 3 and 9 carry the transgene. This DNA fragment was liberated from the transgene by the HindIII digestion. The two last tracks correspond to positive controls in which the complete construct (+C-intact) and the construct digested by HindIII (+C-HindIII) are revealed by bands at 6.3 kb and 5.2 kb respectively.

hGH Determination in Semen by Radioimmunoassay

Figure 3:
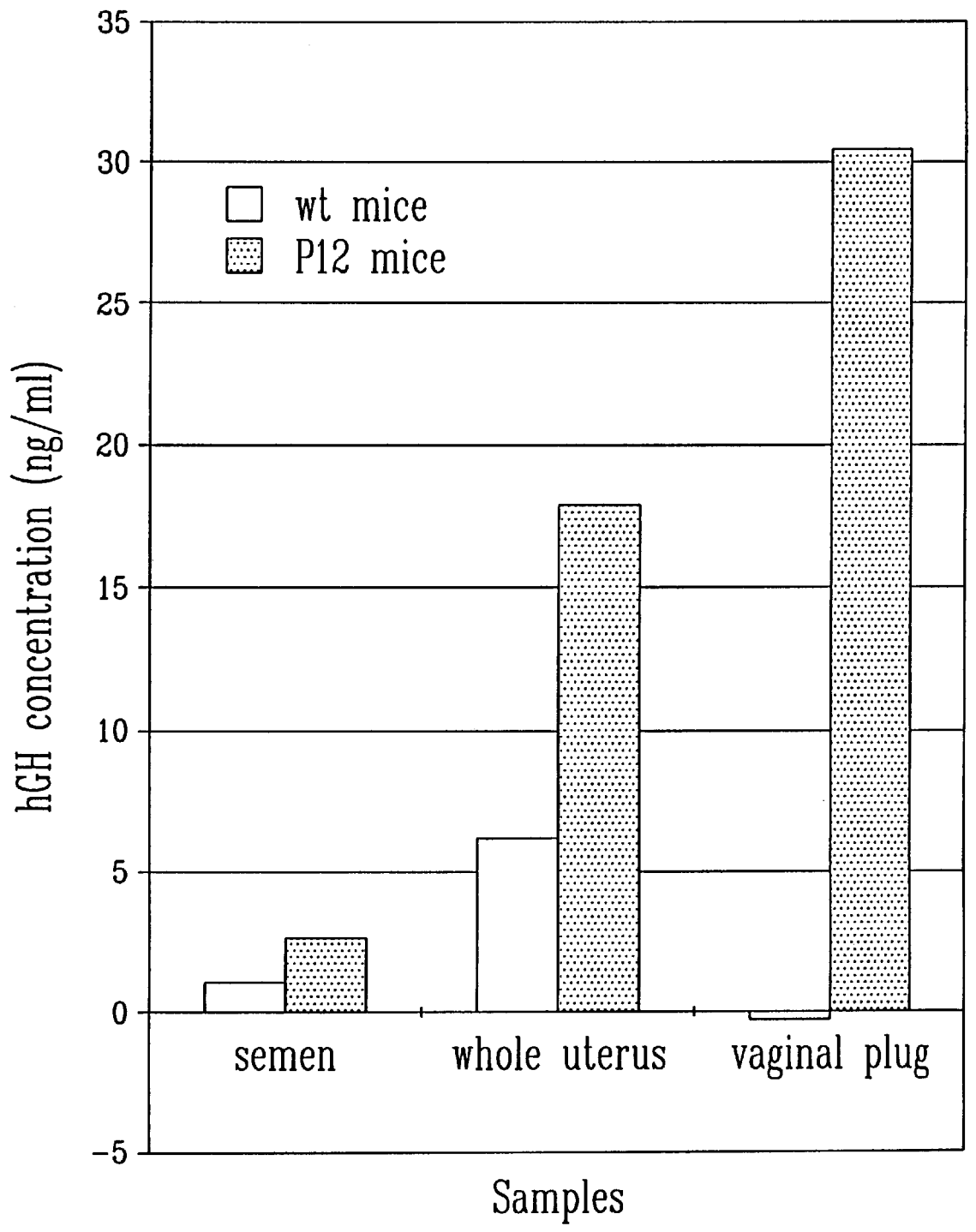
FIG. 3 illustrates the recombinant hGH assay with samples from p12-hGH transgenic mice and wt controls.

In order to determine if the transgene was active, the transgenic male #1 (high number of copies) was mated with a wild type female B6C/3F1. In parallel, a wild type male B6C/3F1 was mated with a wild type female B6C/3F1. Twelve hours following copulation the females were sacrificed and the vaginal plug, uterine content and the complete uterus were collected for analysis of the hGH content. Concentrations of hGH were determined by radioimmunoassay (RIA) using a hGH specific kit (Immunocorp, Montreal, Canada) according to the manufacturer's instructions. This process makes it possible to measure very low concentrations (0.01 ng) of hGH in small volumes. In the mouse, the content of the seminal vesicles solidifies and forms a vaginal plug at the time of ejaculation. This reaction prevents the sperm from flowing out the uterus after copulation. The size of the plug is generally 4 mm×3 mm. The content of the uterus, the plug and the uterine tissues were analyzed individually. The results are presented in FIG. 3. The uterine contents after mating with the transgenic male (secretions coming mostly from prostate) shows a concentration of 2.53 ng/ml. The whole uterus from the same female (uterus cells dissociated by mechanical means) shows an average of 18 ng/ml of hGH. Finally, the vaginal plug produced after mating with the transgenic male contains a concentration of 30.44 ng/ml of hGH. Since the p12 promoter used in the construct is active mostly in the seminal vesicles, we anticipated that the highest concentration of hGH would be found in the plug.

Conclusion

These experiments were designed to prove that it is possible to use the genital tract and the accessory glands of the male to synthesize recombinant proteins. This first set of experiments clearly illustrates that a human peptide, (hGH) not normally found in mouse semen, has been newly synthesized at a significative concentration in the semen of the transgenic animal. Characterization of the other transgenic mice is under way.

The same experiment could be conducted in pigs with modifications in regard to the protocol of superovulation and the surgeries required for the collection and the transfer of the pig embryos.

It should be understood that this is one specific example designed to illustrate the technology. Although the targeted tissues are components of the genital tract, one can use other regulatory sequences or cDNA or genes to be expressed using the same methodology.

EXAMPLE II

Methods for Improving Spermatozoa Viability and Semen Storage

In accordance with one embodiment of the present invention, a non-human transgenic animal secreting a protein including, without limitation, catalase, in its semen has an increased sperm viability and semen storage.

The following demonstration about the protein catalase is described in U.S. patent application Ser. No. 08/802,271 filed on Feb. 19, 1997 in the name of Universite Laval, also the owner of the above-noted application, the content of which is hereby incorporated by reference.

Hydrogen peroxide ($H_2O_2$) is a highly reactive oxygen species which is one of the most toxic compound to sperm. $H_2O_2$ not only inhibit the livability, but also the acrosome reaction, the sperm binding with the egg and oocyte penetration. The oviductal catalase activates the decomposition of $H_2O_2$ in water and oxygen, thus breaking the chain reaction of free radical production leading to lipid peroxidation. The catalase activity in oviductal fluid increased during the cycle, to reach its maximal activity just before ovulation (days 18–20). No significant difference in the activity was seen between the fluid from isthmus or ampulla. Immunoaffinity column against bovine liver catalase, or direct addition of the antibody, did remove all catalase activities from the oviductal fluid. Purification of the oviductal fluid catalase was achieve by its elution from the immunoaffinity column. Indirect immunostaining of spermatozoa incubated in the oviductal fluid revealed a intense brown staining on the acrosomal cap.

Since $H_2O_2$ is a key product in the chain reaction of free radical production, this new enzyme could be the foremost important product of the female tract for sperm survival. Because this enzyme binds to spermatozoa, it could be use to protect the sperm cells when they are thaw up until they are used to fertilize.

Collection and Preparation of Oviductal Fluid

Oviducts from estrous, metestrous and proestrous cows (four of each) were transported from the slaughterhouse to the laboratory on ice, and dissected free from other tissues. Depending of the experiment, the isthmus was separated from the ampulla. Oviductal cells were extracted by compressing the oviducts with a glass slide and the mucosal tissue was rinsed in Tris-EDTA (40 mM, 1 mM) buffer. The cells were incubated twice for 30 min at 37° C. then centrifuged (10 min, 1500×g) and the supernatant reserved each time. The pooled supernatant (containing oviductal secretions only) was then centrifuged (15 min, 20000×g) filtered (0.45 $\mu$m) and frozen for further experimentation. Four different pools were constituted.

Effect of the Binding of OFP on the Maintenance of Sperm Motility

Figure 4:
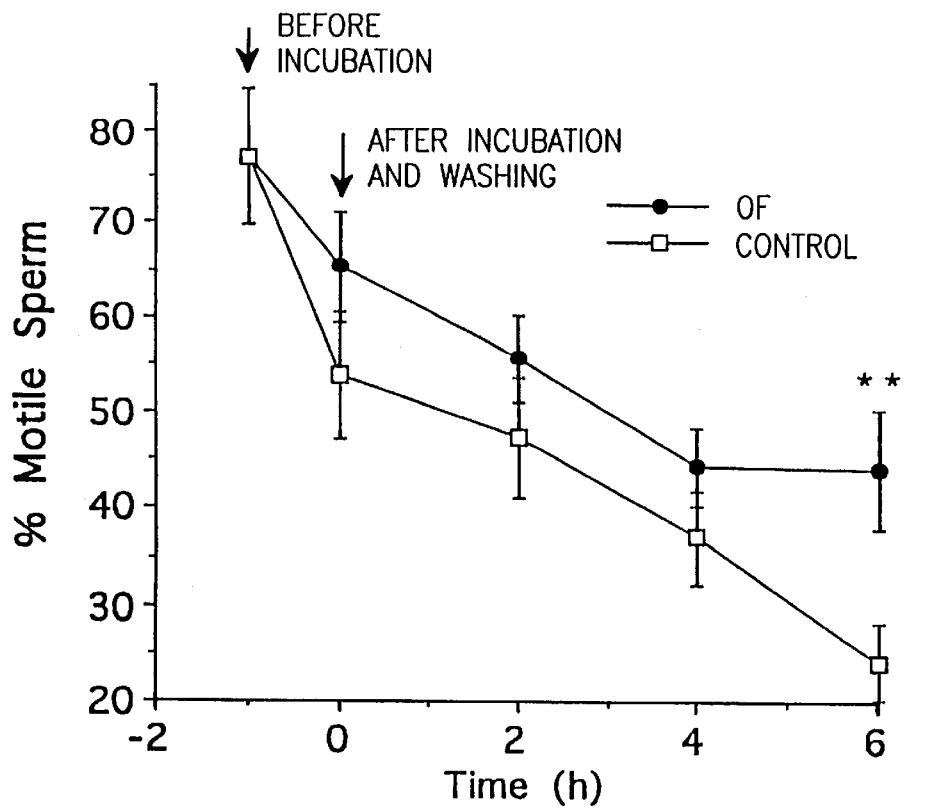
FIG. 4 is a graph of sperm motility measurements following preincubation with bovine oviductal fluid (OF)

FIG. 4 represent a graph of sperm motility measurements following preincubation with oviductal fluid (OF). Freshly washed sperm were preincubated in the presence or absence of OF, washed then incubated for 6 h in TCM-199. The motility was then recorded with a Hamilton-Thorne motility analyzer. Results are means (±SEM) of 3 independent experiments (** $P<0.01$; FIG. 4).

Since only some proteins from OF bind to sperm membranes, this experiment was performed to investigate whether this binding affects the maintenance of sperm motility. This figure shows that after a short 30 min incubation in presence of calcium and one wash, survival was better in presence of oviductal fluid (time 0). This difference is not significant compare to control for the first 4 h (P>0.5), but this trend was maintained through 6 h, at which time the percentage of motile sperm incubated in control media dropped dramatically (23.8%±5.7) whereas that of sperm incubated with OF remained at a higher level (44.2%±6.3, P<0.01). These data suggest a possible association between binding of specific proteins to sperm and the subsequent prolongation of sperm viability.

Catalase Activity in the Oviduct

In culture medium containing specific amino acids, high $H_2O_2$ concentration are present. Since this negative effect could be eliminated by in vitro oviductal secretions, or only by a preincubation of sperm in oviductal fluid (FIG. 4), we suspected a catalase activity in bovine oviductal fluid.

Figure 5:
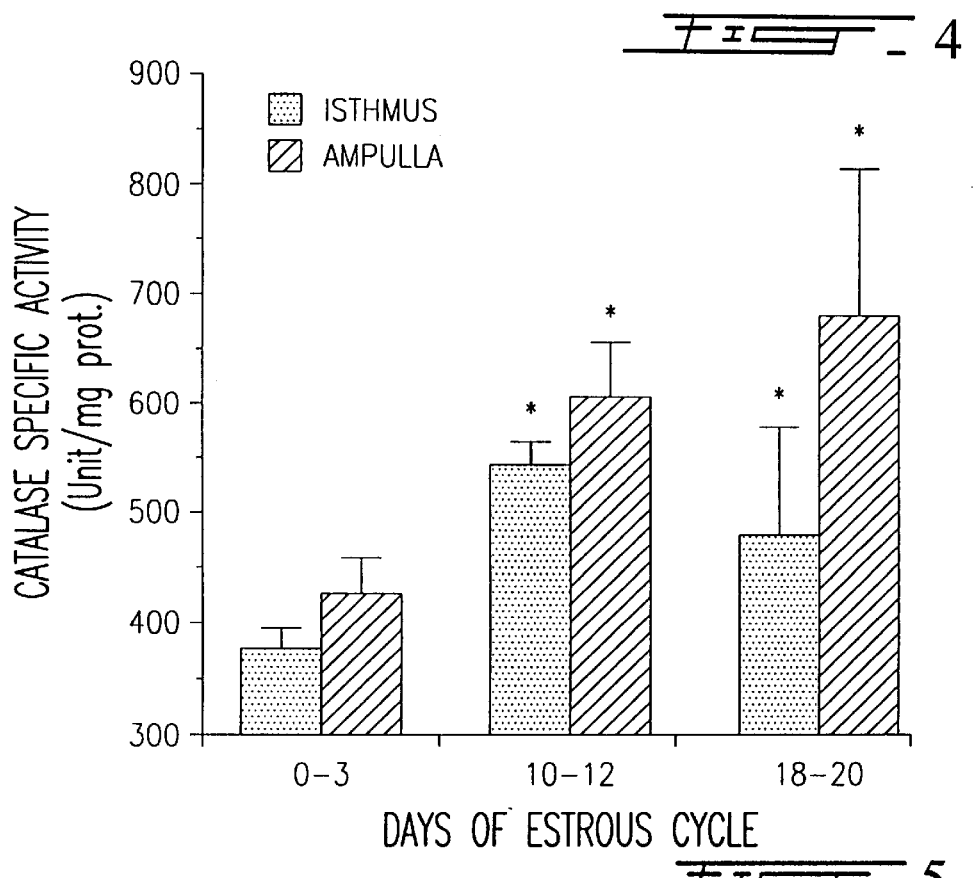
FIG. 5 is a graph of assay of the catalase activity found in the bovine oviductal fluid.

The presence of a catalase activity in that fluid is shown in FIG. 5. Tubal cells were harvested and washed to obtain the fluid. Determination of the catalase activity was mesured twice by the diparition of $H_2O_2$ at 240 nm with a spectrophotometer. Results are means (±SEM) of 4 independent experiments (* P<0.05 from days 0–3; FIG. 5).

Catalase specific activity increased in the fluid during the estrous cycle, to reach maximal activity just before ovulation (days 18–20). Fluid from pre-ovulatory oviduct showed large variations in the catalase specific activity. In two experiments the level were as low a fluid from day 0–3, while in two others experiments the catalase specific activity was twice superior. Although the catalase activity in the ampulla was always above than the isthmus, this difference was not significant (P=0.081).

Neutralization of the Catalase Activity

To further prove the presence of a catalase activity in the bovine oviductal fluid, a purified IgG fraction from rabbit serum, directed against a catalase from bovine liver, was used to neutralize the oviductal catalase activity. A immunoaffinity column coupled with the anti-catalase removed 100% of the original catalase activity found in the fluid. Direct addition of the antibody in the oviductal fluid also removed the activity in a dose dependent-manner, as seen in Table 3.

TABLE 3

Effect of the addition of an anti-catalase on the catalase activity in the oviductal fluid

| Antibody added | Residual catalase activity |
|---|---|
| None | 100% |
| 1/1000 | 31% |
| 1/500 | 22% |
| 1/300 | 14% |
| 1/200 | 9% |
| 1/100 | 6% |

Purified IgG fraction from rabbit serum, directed against a catalase from bovine liver, was diluted at various concentration, and incubated for 90 min at 37° C. The residual catalase activity in the oviductal fluid was then assayed as described above.

Purification of the Catalase Activity

Immunoaffinity purification of the oviductal catalase activity was successfull. Fractions eluted from the column were highly active, while no activity remained in the oviductal fluid passed through the column. The purify fraction showed a single band in the 60 kDa area on SDS page electrophoresis (bromophenol blue coloration).

In Semen Extenders

A purified catalase (OFC) is added to the semen extenders destined to crypreservation or fresh semen conservation before sperm addition. Protective effects starts immediately by removing toxic $H_2O_2$ from the solution and continue in the presence of spermatozoa. For semen destined to cryopreservation, allow 30–60 min. at room temperature before freezing to permit to the OFC to interact and bind to the spermatozoa membranes.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A method for the production of a heterologous protein in semen of a mouse comprising the steps of:

production a transgenic mouse whose genome comprises an expression system comprising in operable association a p12 promoter, a DNA sequence encoding a signal peptide and a DNA sequence encoding a protein heterologous to the promoter, wherein expression of said DNA sequences results in the production and secretion of said protein of interest into the mouse's semen to a detectable level; and collecting semen produced by said transgenic mouse.

2. The method according to claim 1, wherein said expression system further comprises a 3' untranslated regions downstream of the DNA sequence encoding said heterologous protein.

3. The method according to claim 1, wherein said expression system further comprises a 5' untranslated regions between said promoter and said DNA sequence encoding a signal peptide.

4. The method according to claim 1, wherein said promoter is selected from the group consisting of p12, p25, kallikreins, PSA, SBP-C and secretory protein IV promoters.

5. The method according to claim 1, wherein said recombinant protein is selected from the group consisting of, catalase, mono- and bi-specific antibodies, immunoglobulins, cytokines, coagulation factors, tissue plasminogen activator, GM-CSF, erythropoietin, thrombopoietin, alpha-1 antitrypsin, animal growth hormones, cell surface proteins, insulin, interferons, lipases, antiviral protein, antibacterial protein, bacteriocins, peptide hormones, lipocortins and epidermal growth factor.

6. A transgenic mouse whose genome comprises in operable association a p12 promoter, a DNA sequence encoding a signal peptide and a DNA sequence encoding a protein heterologous to the promoter, wherein expression of said DNA sequences results in the production and secretion of said protein of interest into the mouse's semen to a detectable level.

* * * * *